United States Patent
Hedmann et al.

(10) Patent No.: US 9,381,289 B2
(45) Date of Patent: Jul. 5, 2016

(54) APPARATUS FOR PERITONEAL DIALYSIS

(75) Inventors: Frank Hedmann, Volkach (DE); Stephan Klatte, Nienburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1773 days.

(21) Appl. No.: 12/493,797

(22) Filed: Jun. 29, 2009

(65) Prior Publication Data

US 2010/0005416 A1    Jan. 7, 2010

(30) Foreign Application Priority Data

Jul. 4, 2008   (DE) .......................... 10 2008 031 660

(51) Int. Cl.
*A61M 1/28* (2006.01)

(52) U.S. Cl.
CPC ........... *A61M 1/28* (2013.01); *A61M 2205/331* (2013.01); *A61M 2205/505* (2013.01); *A61M 2205/52* (2013.01)

(58) Field of Classification Search
CPC   G06F 3/0484; G06F 3/04842; G06F 11/3672
USPC ........................................................ 715/764
See application file for complete search history.

(56) References Cited

U.S. PATENT DOCUMENTS

| | | | |
|---|---|---|---|
| 5,406,310 A * | 4/1995 | Aschenbrenner et al. | 345/602 |
| 5,620,658 A * | 4/1997 | Jaunakais | 422/401 |
| 6,228,047 B1 | 5/2001 | Dadson | |
| 7,704,224 B2 * | 4/2010 | Hamada et al. | 604/29 |
| 7,756,328 B2 * | 7/2010 | Komiya et al. | 382/164 |
| 2002/0045851 A1 * | 4/2002 | Suzuki et al. | 604/28 |
| 2003/0216677 A1 | 11/2003 | Pan et al. | |
| 2005/0131340 A1 * | 6/2005 | Sorenson et al. | 604/29 |
| 2008/0113386 A1 * | 5/2008 | Thadhani et al. | 435/7.1 |
| 2008/0132828 A1 | 6/2008 | Howard | |

FOREIGN PATENT DOCUMENTS

| | | |
|---|---|---|
| EP | 0619135 | 10/1994 |
| EP | 1547516 | 6/2005 |
| JP | 8098882 A | 4/1996 |
| JP | 2001/187027 | 7/2001 |
| JP | 2003047657 A | 2/2003 |
| WO | WO2007023328 A1 | 3/2007 |

* cited by examiner

*Primary Examiner* — Jeffrey A Gaffin
*Assistant Examiner* — Sabrina Greene
(74) *Attorney, Agent, or Firm* — Fish & Richardson P.C.

(57) ABSTRACT

This invention relates to a device for peritoneal dialysis with a means for the regular discharge and reuptake of dialysate, wherein the means includes an agent by which the color and turbidity of the dialysate can be determined.

26 Claims, 3 Drawing Sheets

APPARATUS FOR PERITONEAL DIALYSIS

CROSS REFERENCE TO RELATED APPLICATION

This application claims priority under 35 U.S.C. §119(a) to German Patent Application No. 10 2008 031 660.1, filed Jul. 4, 2008, the entire contents of which are hereby incorporated by reference.

TECHNICAL FIELD

This invention relates to a device for peritoneal dialysis.

BACKGROUND

In peritoneal dialysis (PD), a dialysis solution (dialysate) is introduced into the abdominal cavity of a patient. After a certain dwell time, during which an exchange between the dialysate and blood takes place via the peritoneum of the patient, the now "used" dialysate is replaced by fresh dialysate. For this purpose, the used dialysate usually is drained into a bag. During the dwell time in the abdominal cavity, the color of the dialysate changes. Besides a discoloration of the dialysate, turbidity can frequently be observed. Normally, the dialysate should have the color of apple juice. Upon being drained, the discoloration or turbidity of the used dialysate is subjected to a visual inspection by the physician, the person responsible for the dialysis or the patient himself. By means of the turbidity, it is evaluated whether the used dialysate has a usual, normal discoloration. If the discoloration is classified as being abnormal, further examinations usually are initiated to find out the causes. Discolorations which are not within the expected normal range can indicate various pathological causes, such as an increased secretion of protein, a secretion of blood, or they might for instance indicate early-stage peritonitis (inflammation of the peritoneum). In the case of unusual discolorations, it is recommendable to consult a physician in order to possibly initiate further examinations.

What is problematic in the visual inspection is the subjective perception of the observer, in particular of the untrained patient. Due to subjective and changing criteria for evaluation, the observer cannot always recognize with constant certainty whether the dialysate drained from the abdominal cavity exhibits a comparatively normal or abnormal discoloration.

SUMMARY

It is an object of the invention to develop a device for peritoneal dialysis such that the objectivity of the evaluation of the discoloration or turbidity of the dialysate is improved, and a machine is provided to support the evaluation of the turbidity.

Accordingly, there is provided a device for peritoneal dialysis with a means for the regular discharge and reuptake of dialysate (cycler), which includes a conduit with a catheter. In accordance with the invention, this means includes a device by which the color and turbidity of the dialysate can be determined. Due to this inventive solution, the operator, i.e., the physician, the person responsible for the dialysis or even the patient himself, can determine or arrange for determination of the turbidity of the actual dialysate to be evaluated with objective means.

The color and turbidity values of the dialysate obtained by such means can be storable. For this purpose, the color and turbidity values can be storable in a memory provided in the means.

In accordance with another advantageous aspect, the color and turbidity values together with alphanumeric data, for instance the patient data, can be storable on a removable storage medium, for instance a memory chip on the patient card.

The means for determining color and turbidity advantageously can include a display, preferably in the form of a touch screen. On the display, a color spectrum can be represented, from which the color and turbidity applicable can be selected by the operator. For this purpose, the color and turbidity can be represented on the display in an especially provided window and can be selected therefrom. To provide for a direct comparison between the dialysate and the color scale indicated on the display, it is particularly advantageous when an illumination field is provided on the display, by means of which a drainage conduit or cuvette, which are each filled with dialysate, can be illuminated. By means of the color and turbidity value of the dialysate obtained, the operator can select and enter the appropriate value within the resulting scale of color and turbidity values represented on the display.

On the display, the device preferably can include an alarm field, which issues an alarm in the case of a predetermined deviation of the determined color and turbidity value from a specified color and turbidity value. This alarm can be issued on the display merely as a visual alarm. Alternatively, however, it is also conceivable that an additional acoustic alarm bell or some other alarm signal will sound. Possibly, an acoustic alarm signal can be output alone without any indications on the display. Issuing of an alarm prompts the user to consult a physician, who could then make further examinations.

In accordance with a preferred aspect, the color and turbidity values of past measurements could be indicated on the display in a comparison. From the history of turbidity and from the stored turbidity and color values, the physician can obtain a clue as to existing complications and thus can arrange for a specific examination.

This invention also relates to a corresponding method of determining the color and turbidity of dialysate.

DESCRIPTION OF DRAWINGS

Further details and advantages of the invention will be explained in detail with reference to embodiments illustrated in the drawings, in which.

DETAILED DESCRIPTION

Figure 1:
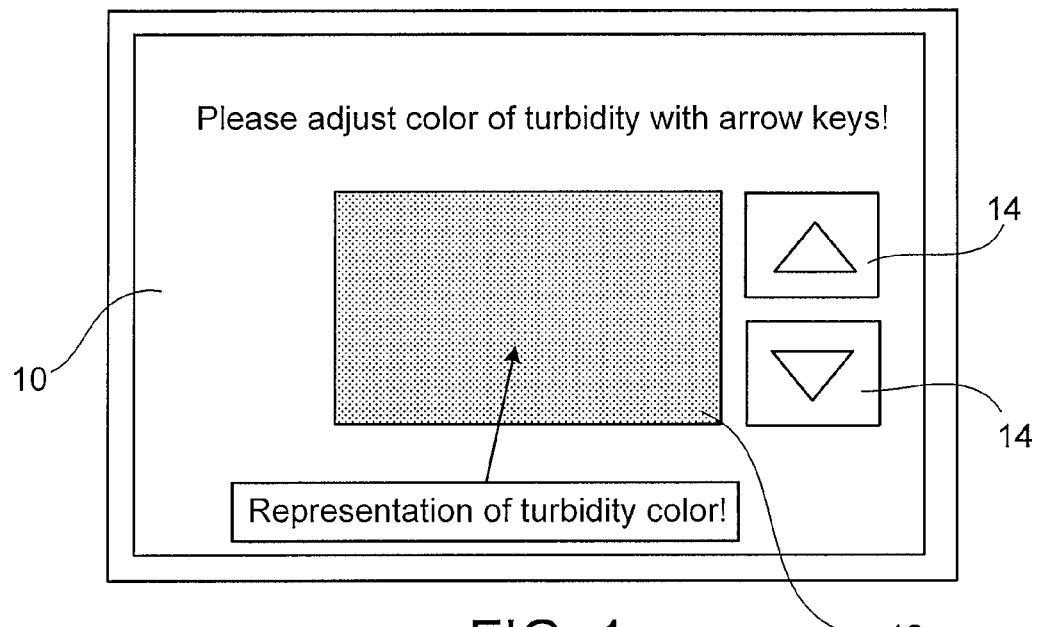
FIGS. 1-5: show different configurations of a display of a device in accordance with the invention.

FIG. 1 shows a display 10, which can be provided on a means for the regular discharge and reuptake of dialysate in a device for peritoneal dialysis. By means of this display, the color of the dialysate drained after a peritoneal dialysis treatment can be determined. For this purpose, a window 12 is provided on the display 10, which constitutes a touch screen. In the window 12, a typical color and a typical degree of turbidity are represented, which can correspond to the color of a "used" dialysate. Via the arrow keys 14, which can activated by touching the touch screen, the operator (i.e., the physician, the person responsible for the dialysis or the patient himself) can change the color value from a corresponding scale, which is stored in a memory associated with the display 10, in order to thus select that value that corresponds to the actual color or the actual degree of turbidity of the dialysate. When noting a correspondence between the color represented in the window 12 or the represented degree of turbidity and the dialysate, the value indicated there can be stored by touching the window 12. When a simple display 10 (i.e., a display without a touch screen) is provided, the operability explained here with reference to a touch screen can be realized by other input means, such as a usual computer keyboard or a computer mouse.

Figure 2:
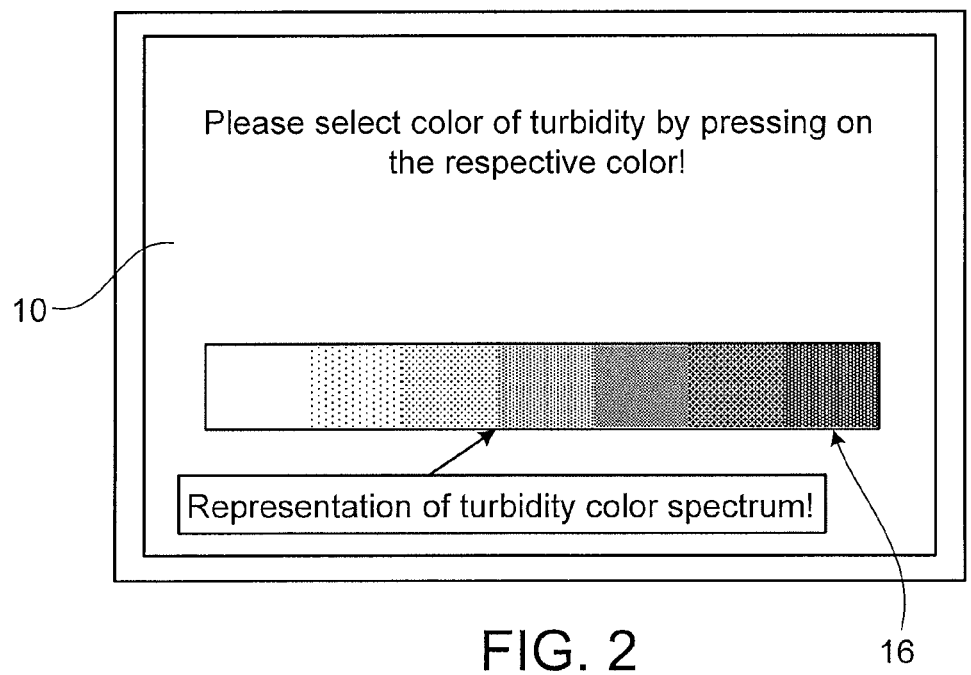

FIG. 2 shows an alternative variant, in which the display 10 not only indicates a specific color and turbidity value in its output window 16, but an entire spectrum of turbidity colors. When the display is configured as a touch screen, the value can be selected and stored by touching the spectrum in the color and turbidity range which corresponds to that of the dialysate.

Figure 3:
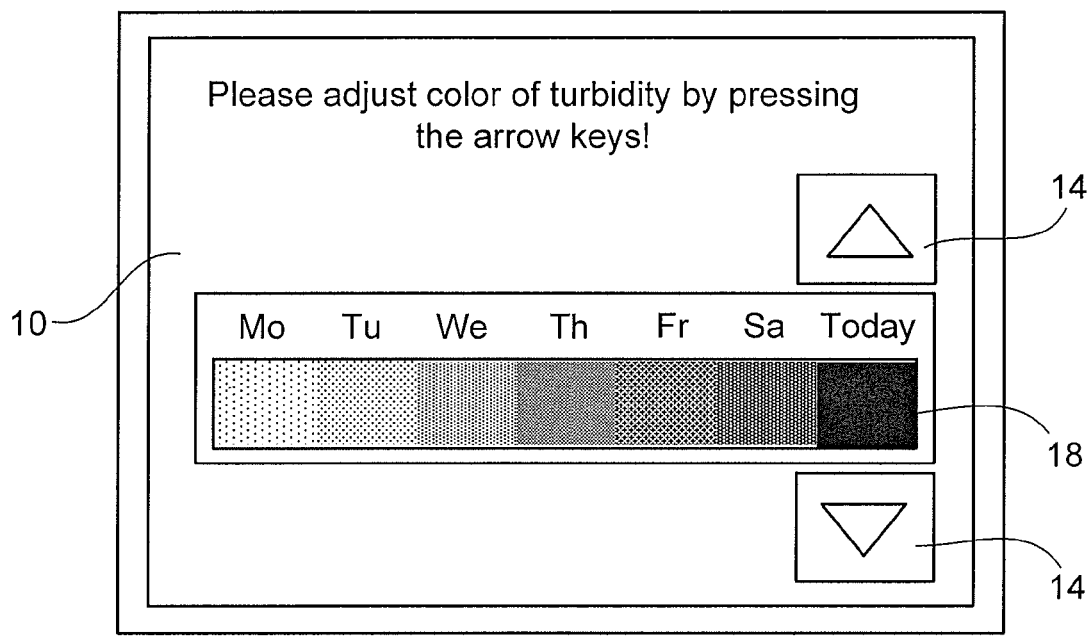

Another alternative configuration of a display, which has a slightly different mode of operation, is shown in FIG. 3. Similar to the variant shown in FIG. 1, the value actually detected for the dialysis treatment is entered in a window 18 via arrow keys 14 provided on the touch screen. By means of an internal memory, this value then is stored and on the following day is indicated under the corresponding weekday in the window 16, so that in the illustrated embodiment a weekly history is obtained. The weekly history provides the attending physician with information about possible changes of the dialysate and hence allows the same to infer possibly existing pathological changes.

Figure 4:
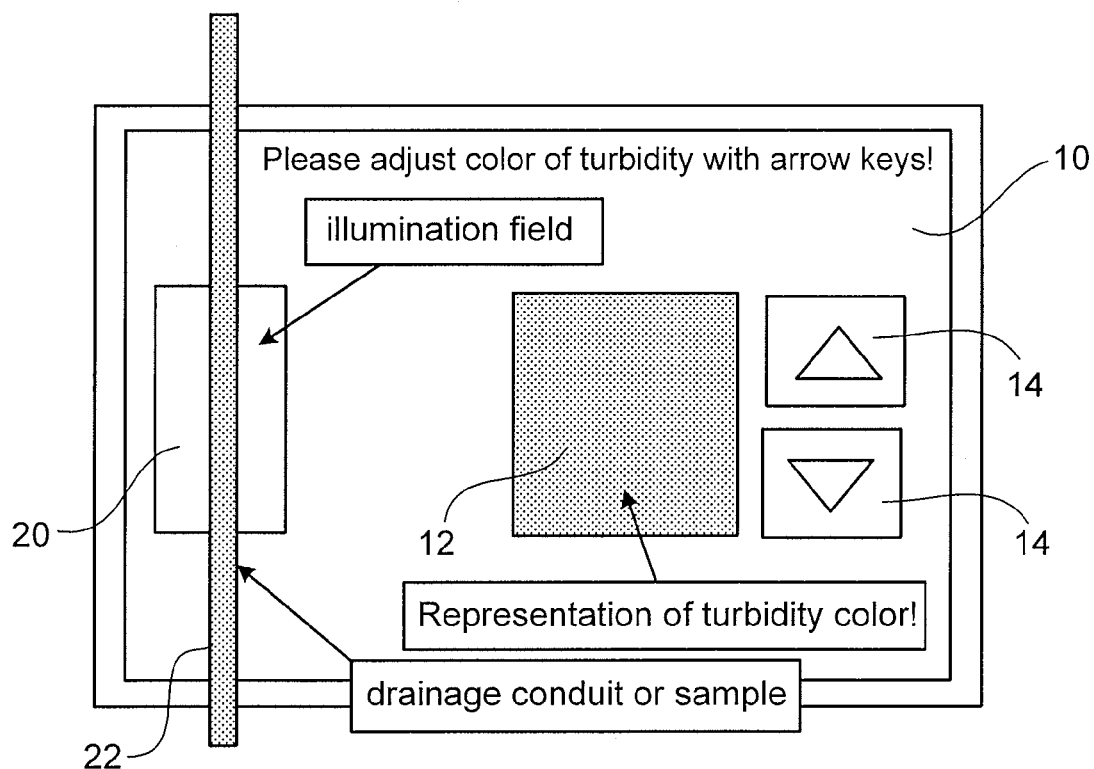

In FIG. 4, a display 10 is shown, which in its right part substantially corresponds to the embodiment shown in FIG. 1 and has corresponding functionality. To be able to directly compare the dialysate, an additional illumination field 20 is provided in the display, in front of which a transparent drainage conduit 20 is provided in the embodiment shown. Due to its transparency, the drainage conduit 20 provides for transillumination. Thus, the discoloration of the dialysate passed through this drainage conduit or the degree of turbidity thereof can directly be compared by the operator with the representation of the color or the degree of turbidity selected in the window 12. The determination of the actual color and turbidity value of the dialysate largely is objectified thereby.

Figure 5:
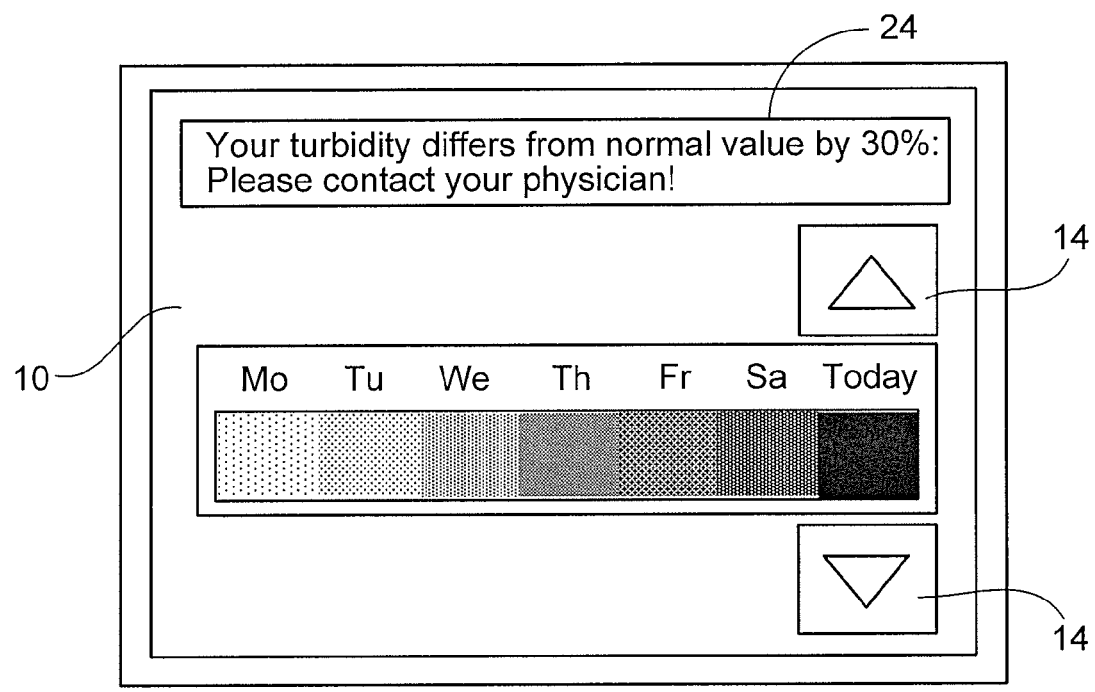

In the representation of FIG. 5, a variant of a display 10 is shown, which largely corresponds to that of FIG. 3. However, an additional alarm display field 24 is provided on the display 10. An alphanumeric alarm signal can be issued by the display field 24 when the actually detected color or turbidity value of the dialysate differs from the specified turbidity value beyond a predetermined extent. Optionally, this optical alphanumeric alarm display can also be supported acoustically.

The invention claimed is:

1. A peritoneal dialysis device, comprising:
    a drainage conduit configured to receive used dialysate from a patient; and
    a display, wherein
        a portion of the drainage conduit is positionable at a location adjacent a region of the display, and
        the peritoneal dialysis device is configured to display a plurality of colors in a designated window on the region of the display, the plurality of colors corresponding to a plurality of turbidity levels of dialysate,
        wherein the peritoneal dialysis device is configured such that a color currently displayed in the designated window on the display can be selected for input into the peritoneal dialysis device as a color that most closely corresponds to a color of the used dialysate in the portion of the drainage conduit, and
        wherein the peritoneal dialysis device is configured to operate according to at least one of: a) at least first and second colors of the plurality of colors are simultaneously displayed in the designated window on the display for selection and b) a first color of the plurality of colors is displayed in the designated window on the display for selection and can be changed to at least a second color of the plurality of colors.

2. The device of claim 1, wherein the peritoneal dialysis device is configured to store a color selected by a user.

3. The device of claim 2, wherein the peritoneal dialysis device comprises memory for storing the color selected by the user.

4. The device of claim 2, wherein the peritoneal dialysis device comprises a removable storage medium on which the color selected by the user is stored together with alphanumeric data.

5. The device of claim 4, wherein the removable storage medium comprises a memory chip, and the alphanumeric data comprises patient data.

6. The device of claim 1, wherein the display is in the form of a touch screen.

7. The device of claim 1, wherein the display comprises an illumination field configured to illuminate the used dialysate in the drainage conduit.

8. The device of claim 1, wherein the peritoneal dialysis device is configured to emit an alarm when the color selected by the user differs from a theoretical color by a certain degree.

9. The device of claim 8, wherein the alarm is a visual alarm displayed in an alarm field of the display.

10. The device of claim 1, wherein the peritoneal dialysis device is configured to simultaneously display in a second designated window on the display a plurality of colors previously selected by a user of the peritoneal dialysis device and stored on a storage medium.

11. A peritoneal dialysis method, comprising:
    displaying a plurality of colors in a designated window on a region of a display of a peritoneal dialysis device, the plurality of colors corresponding to a plurality of turbidity levels of dialysate, wherein a) at least first and second colors of the plurality of colors are simultaneously displayed in the designated window on the display for selection by a user or b) a first color of the plurality of colors is displayed in the designated window on the display for selection by a user and can be changed to at least a second color of the plurality of colors;
    positioning a drainage conduit at a location adjacent to the region of the display, the drainage conduit being configured to receive used dialysate from a patient;
    comparing a color of used dialysate within the drainage conduit to the plurality of colors displayed on the region of the display;
    selecting, by input into the peritoneal device, a color from the plurality of colors displayed on the region of the display that most closely corresponds to a color of the used dialysate within the drainage conduit; and
    storing the selected color in the peritoneal dialysis device.

12. The method of claim 11, wherein the selected color is stored in memory of the peritoneal dialysis device.

13. The method of claim 11, wherein the selected color is stored on a removable storage medium of the peritoneal dialysis device.

14. The method of claim 11, wherein the selected color is stored together with alphanumeric values.

15. The method of claim 14, wherein the alphanumeric values comprise patient data.

16. The method of claim 11, further comprising displaying a color spectrum on the display, wherein the selected color is one of multiple colors on the color spectrum.

17. The method of claim 11, further comprising illuminating the used dialysate in the drainage conduit in order to allow the user to select the displayed color that most closely corresponds to the color of the used dialysate.

18. The method of claim 11, further comprising emitting an alarm when the color selected by the user differs from a theoretical color by a certain degree.

19. The method of claim 11, further comprising displaying a plurality of previously selected colors on the display.

20. The method of claim 11, further comprising:
selecting a turbidity level displayed on the display of the peritoneal dialysis device that most closely corresponds to a turbidity of the used dialysate exiting the peritoneal dialysis device; and
storing the selected turbidity level in the peritoneal dialysis device.

21. The device of claim 1, wherein the display comprises an illumination field configured to illuminate the used dialysate in the drainage conduit, the illumination field being disposed at a location adjacent the region of the display used to display the plurality of colors.

22. The method of claim 11, further comprising
positioning the drainage conduit over an illumination field on the display, the illumination field configured to illuminate the used dialysate in the drainage conduit; and
illuminating the used dialysate in the drainage conduit via the illumination field in order to allow the user to select the displayed color that most closely corresponds to the color of the used dialysate.

23. The device of claim 1, wherein the color currently displayed in the designated window can be selected for input by at least one of pressing a button, touching an area of the display operating as a touch screen, using a keyboard, and using a mouse.

24. The device of claim 1, wherein the at least first and second colors are simultaneously displayed in the designated window and can be input for selection by at least one of pressing a button, touching an area of the display operating as a touch screen, using a keyboard, or using a mouse.

25. The device of claim 1, wherein the first color is displayed in the designated window on the display and can be input for selection by at least one of pressing a button, touching an area of the display operating as a touch screen, using a keyboard, and using a mouse, wherein the first color can be changed to at least a second color of the plurality of colors of a color spectrum by at least one of pressing a button, touching an area of the display operating as a touch screen, using a keyboard, and using a mouse.

26. The device of claim 1, wherein the display is in the form of a touch screen, and the at least first and second colors are simultaneously displayed at first and second positions in the designated window on the touch screen, and selectable by a user by touching the touch screen in the first and second positions, respectively.

* * * * *